(12) United States Patent
Vermilyea et al.

(10) Patent No.: US 10,684,336 B2
(45) Date of Patent: Jun. 16, 2020

(54) RADIOFREQUENCY COIL AND SHIELD IN MAGNETIC RESONANCE IMAGING METHOD AND APPARATUS

(71) Applicant: General Electric Company, Schenectady, NY (US)

(72) Inventors: Mark Ernest Vermilyea, Schenectady, NY (US); Justin Michael Ricci, Schenectady, NY (US); Christina Vasil, Troy, NY (US); Ek Tsoon Tan, Halfmoon, NY (US); Eric William Fiveland, Schenectady, NY (US); Yihe Hua, Rexford, NY (US); Thomas Kwok-Fah Foo, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/169,536

(22) Filed: Oct. 24, 2018

(65) Prior Publication Data

US 2020/0132792 A1  Apr. 30, 2020

(51) Int. Cl.
  *G01R 33/422* (2006.01)
  *G01R 33/385* (2006.01)
  *A61B 5/055* (2006.01)
  *G01R 33/34* (2006.01)

(52) U.S. Cl.
  CPC .......... *G01R 33/422* (2013.01); *A61B 5/055* (2013.01); *G01R 33/3403* (2013.01); *G01R 33/34092* (2013.01); *G01R 33/3856* (2013.01)

(58) Field of Classification Search
  CPC .............. G01R 33/543; G01R 33/5608; G01R 33/4828; G01R 33/3415; G01R 33/283; G01R 33/307; G01R 33/422; G01R 33/3403; G01R 33/34092; G01R 33/3856; A61B 5/055
  USPC .......................... 324/307, 309, 318, 322, 314
  See application file for complete search history.

(56) References Cited

U.S. PATENT DOCUMENTS

| | | | |
|---|---|---|---|
| 5,406,204 A * | 4/1995 | Morich | G01R 33/3815 324/318 |
| 5,610,521 A * | 3/1997 | Zou | G01R 33/34 324/318 |
| 7,047,062 B2 | 5/2006 | Licato et al. | |
| 7,259,560 B2 * | 8/2007 | Yamanaka | G01R 33/28 324/307 |
| 7,719,277 B2 | 5/2010 | Eberler et al. | |

(Continued)

OTHER PUBLICATIONS

Parker, Dennis L., et al.; "Multiple-region gradient arrays for extended field of view, increased performance, and reduced nerve stimulation in magnetic resonance imaging", Magnetic resonance in medicine, vol. 56, Issue: 6, pp. 1251-1260, Dec. 2006.

(Continued)

*Primary Examiner* — Jermele M Hollington
*Assistant Examiner* — Taqi R Nasir
(74) *Attorney, Agent, or Firm* — Fletcher Yoder, P.C.

(57) ABSTRACT

An imaging device may include a patient bore to house a subject to be imaged, wherein the patient bore includes one or more bore tubes. The imaging device may also include a gradient coil surrounding, at least partially, the patient bore and a radio frequency (RF) shield located outside the one or more bore tubes. Additionally, the imaging device may include an RF coil located within at least one of the bore tubes.

20 Claims, 6 Drawing Sheets

(56) References Cited

U.S. PATENT DOCUMENTS

| | | |
|---|---|---|
| 7,728,590 B2 | 6/2010 | Eberler et al. |
| 8,131,340 B2 | 3/2012 | Eberlein et al. |
| 9,220,893 B2 | 12/2015 | Hegland et al. |
| 9,869,735 B2 | 1/2018 | Leussler et al. |
| 2008/0129292 A1* | 6/2008 | Leussler .......... G01R 33/34046 324/318 |
| 2008/0186026 A1* | 8/2008 | Leussler ............. G01R 33/422 324/318 |
| 2008/0272784 A1 | 11/2008 | Harvey et al. |
| 2009/0128150 A1* | 5/2009 | Ham ................ G01R 33/34076 324/318 |
| 2011/0015078 A1 | 1/2011 | Gao et al. |
| 2015/0102813 A1* | 4/2015 | Dumoulin .............. G01R 33/34 324/322 |
| 2015/0346297 A1* | 12/2015 | Naka .................. G01R 33/3858 324/322 |

OTHER PUBLICATIONS

Lazar, R. et al.; "Integrated RF Birdcage Head Coil* for 7T MRI", Magnetic resonance in medicine, vol. 15, 2007.

* cited by examiner

RADIOFREQUENCY COIL AND SHIELD IN MAGNETIC RESONANCE IMAGING METHOD AND APPARATUS This invention was made with Government support under contract number W81XWH-16-2-0054 awarded by the Department of Defense. The Government has certain rights in the invention.

BACKGROUND

In general, magnetic resonance imaging (MRI) examinations are based on the interactions among a primary magnetic field, a radiofrequency (RF) magnetic field, and time varying magnetic gradient fields with gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

During imaging sequences, the time varying gradient fields are generated by application of current to a series of gradient coils. Additionally, RF fields are generated simultaneously with the gradient fields by application of current to RF coils. RF shielding on the outside of the RF coils may help reduce direct interaction between the gradient coils and the RF coils as well as shield external components and/or the environment from electromagnetic interference. However, the positioning of the RF coils and/or shielding may cause issues concerning efficiency as well as patient comfort.

BRIEF DESCRIPTION

In one embodiment, an imaging device may include a patient bore to house a subject to be imaged, wherein the patient bore includes one or more bore tubes. The imaging device may also include a gradient coil surrounding, at least partially, the patient bore and a radio frequency (RF) shield located outside the one or more bore tubes. Additionally, the imaging device may include an RF coil located within at least one of the bore tubes.

In another embodiment, a patient bore designed to surround a subject for imaging may include a shield support tube and a coil support tube removably insertable into the shield support tube. The patient bore may also include a radio frequency (RF) coil mounted to an outer surface of the coil support tube and an RF shield mounted to an outer surface of the shield support tube. The RF shield may reduce RF interference to or from the RF coil.

In another embodiment, a magnetic resonance imaging system may include a patient bore to house a subject. The patient bore may include a shield support tube and a coil support tube removably insertable into the shield support tube. The patient bore may also include an RF coil to generate an RF signal, wherein the RF coil is mounted on the surface of the coil support tube. The patient bore may also include an RF shield to attenuate the RF signal, wherein the RF shield is mounted to the surface of the shield support tube. The system may also include a gradient coil to generate a magnetic field. The gradient coil may also have a cavity within to house the patient bore. The RF signal, the magnetic field, or a combination thereof may operatively cause an excitation within the subject, wherein the excitation is measured by the system to compute an image corresponding to the subject.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
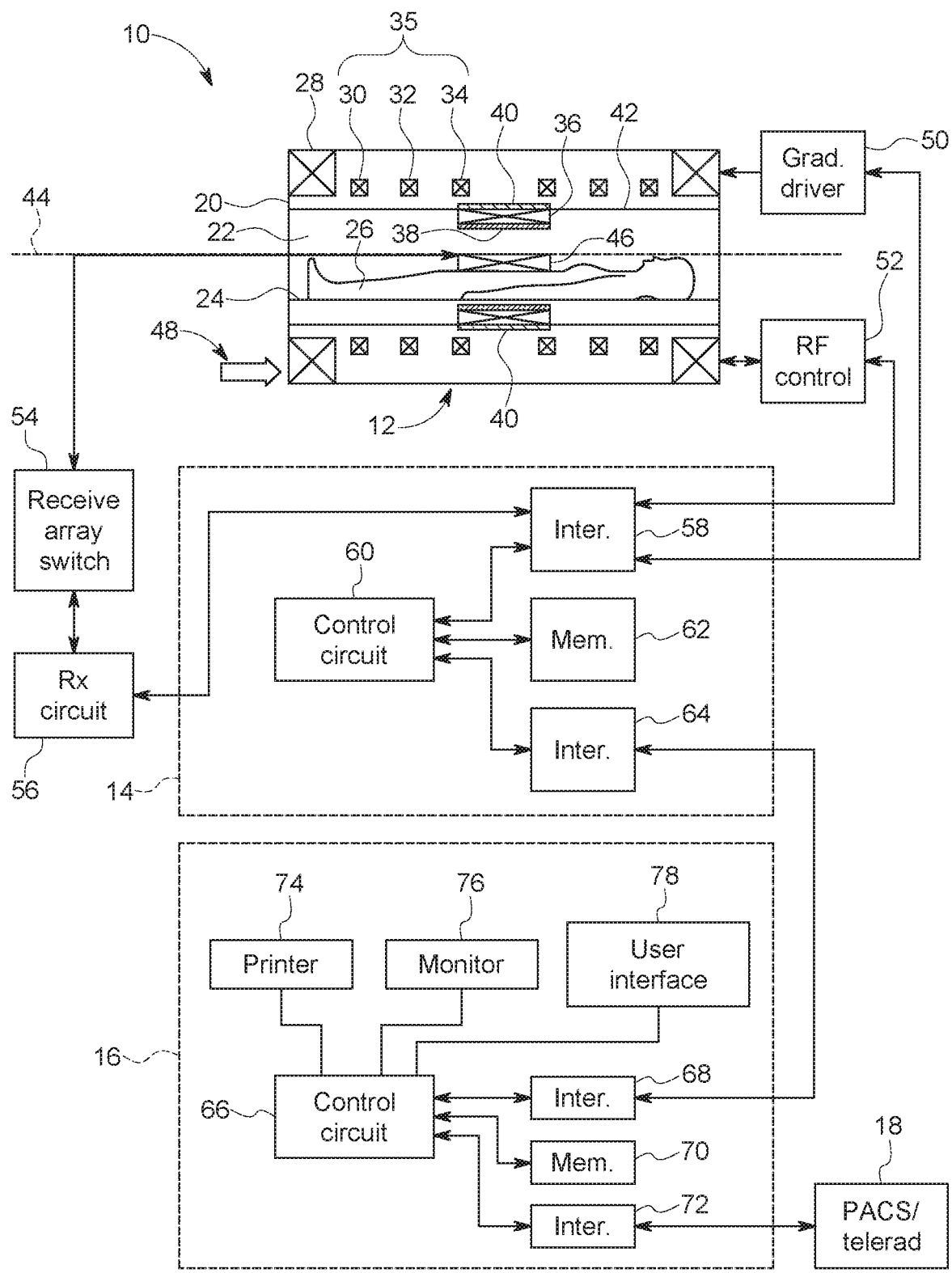
FIG. 1 illustrates a magnetic resonance imaging (MM) system having gradient coils, radio frequency (RF) coils, and RF shielding, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In general, magnetic resonance imaging (MRI) is based on the interactions of a primary magnetic field, time varying magnetic gradient fields, and a radiofrequency (RF) field with gyromagnetic material within a subject of interest (e.g., a patient). Certain gyromagnetic materials, such as hydrogen nuclei in water molecules, have characteristic behaviors in response to external electromagnetic fields (e.g., constant or time varying electric fields, magnetic fields, or a combination thereof). The precession of spins of these nuclei can be influenced by manipulation of the fields to produce RF signals that can be detected, processed, and used to reconstruct a useful image.

In certain configurations, the subject of interest is placed in a patient bore surrounded by RF coils and gradient coils to generate the RF and gradient fields, respectively. Generally, the RF coils are placed on the exterior of a bore tube defining the patient bore with an RF shield, and the RF shield is placed between the RF coils and the gradient coils to reduce direct interaction between them and to reduce RF interference with external (e.g., external to the scanner of the MM system) components or devices. The RF coils may also be tuned based on their relative position with the RF shield. In some embodiments, the RF shield is built into the gradient coils or the housing thereof, but this may increase the difficulty of and/or frequency of RF coil tuning, for example, if the RF coils are moved or removed for service, RF coil tuning may be repeated. Additionally, the closer the RF shield is to the RF coils, the less efficient the RF coils are. For instance, field stresses between the RF coils and the RF shield may reduce power efficiency. As such, it is now recognized that increasing the distance between the RF shield and the RF coils may increase the efficiency of the RF coils. In one embodiment of the present disclosure, placing the RF coils on an outer surface of a coil support tube and the RF shield on the outer surface of a separate shield support tube may allow for increased RF coil efficiency, increased patient comfort (e.g., a reduction of peripheral nerve stimulation and/or increased space within the patient bore), and/or reduced difficulty or repetitive tuning.

As set forth above, the embodiments described herein may be implemented as a part of an MRI system, wherein specific imaging routines are initiated by a user (e.g., a radiologist). Thus, the system may perform data acquisition, data construction, and in certain instances, image synthesis. Accordingly, referring to FIG. 1, a magnetic resonance imaging system 10 is illustrated schematically as including a scanner 12, scanner control circuitry 14, and system control circuitry 16.

The imaging system 10 additionally includes remote access and storage systems 18 and/or devices such as picture archiving and communication systems (PACS), or other devices such as teleradiology equipment so that data acquired by the imaging system 10 may be accessed on- or off-site. In this way, MRI data may be acquired, followed by on- or off-site processing and evaluation. While the imaging system 10 may include any suitable scanner or detector, in the illustrated embodiment, the imaging system 10 includes a full body scanner 12 having a housing 20 through which an opening (e.g., an annular opening) is formed to accommodate a patient bore 22. The patient bore 22 may be made of any suitable material such as a non-metallic and/or non-magnetic material and generally includes components of the scanner 12 proximate to a subject. A table 24 is moveable into the patient bore 22 to permit a patient 26 to be positioned therein for imaging selected anatomy within the patient 26. As described herein, the patient bore 22 may include one or more bore tubes to support various components of the scanner 12 and/or the patient 26. In some embodiments, the patient bore 22 may support the table 24 and/or articulation components (e.g., a motor, pulley, and/or slides).

The scanner 12 may include a series of associated coils for producing controlled electromagnetic fields for exciting the gyromagnetic material within the anatomy of the subject being imaged. Specifically, a primary magnet coil 28 is provided for generating a primary magnetic field, which is generally aligned with an axis 44 of the patient bore 22. A series of gradient coils 30, 32, and 34 (collectively 35) permit controlled magnetic gradient fields to be generated for positional encoding of certain of the gyromagnetic nuclei within the patient 26 during examination sequences. An RF coil 36 is configured to generate radio frequency pulses for exciting the certain gyromagnetic nuclei within the patient 26. In accordance with an aspect of the present disclosure, the RF coil 36 may be implemented on a coil support tube 38 defining at least a portion of the patient bore 22. Further, an RF shield 40 may be implemented on a shield support tube 42 also defining at least a portion of the patient bore 22 to reduce electromagnetic interference within the imaging system 10, as well as devices separate from the imaging system 10. In addition to the coils that may be local to the scanner 12, the imaging system 10 may also include a set of receiving coils 46 (e.g., an array of coils) configured for placement proximal (e.g., against) to the patient 26. As an example, the receiving coils 46 can include cervical/thoracic/lumbar (CTL) coils, head coils, single-sided spine coils, and so forth. Generally, the receiving coils 46 are placed close to or on top of the patient 26 so as to receive the weak RF signals (e.g., weak relative to the transmitted pulses generated by the scanner coils) that are generated by certain of the gyromagnetic nuclei within the patient 26 as they return to their relaxed state. In some embodiments, the RF coils 36 may both transmit and receive RF signals accomplishing the role of the receiving coils 46.

The various coils of the imaging system 10 are controlled by external circuitry to generate the desired field and pulses, and to read emissions from the gyromagnetic material in a controlled manner. In the illustrated embodiment, a main power supply 48 provides power to the primary magnetic coil 28 to generate the primary magnetic field. A driver circuit 50 may include amplification and control circuitry for supplying current to the coils as defined by digitized pulse sequences output by the scanner control circuitry 14.

An RF control circuit 52 is provided for regulating operation of the RF coil 36. The RF control circuit 52 includes a switching device for alternating between the active and inactive modes of operation, wherein the RF coil 36 transmits and does not transmit signals, respectively. The RF control circuit 52 may also include amplification circuitry to generate the RF pulses. Similarly, the receiving coils 46, or RF coils 36 if no separate receiving coils 46 are implemented, are connected to a switch 54, which is capable of switching the receiving coils 46 between receiving and non-receiving modes. Thus, the receiving coils 46 may resonate with the RF signals produced by relaxing gyromagnetic nuclei from within the patient 26 while in the receiving mode, and avoid resonating with RF signals while in the non-receiving mode. Additionally, a receiving circuit 56 may receive the data detected by the receiving coils 46 and may include one or more multiplexing and/or amplification circuits.

It should be noted that while the scanner 12 and the control/amplification circuitry described above are illustrated as being connected by single lines, one or more cables or connectors may be used depending on implementation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner 12 and the scanner control circuitry 14 and/or system control circuitry 16.

As illustrated, the scanner control circuitry 14 includes an interface circuit 58, which outputs signals for driving the gradient coils 35 and the RF coil 36 and for receiving the data representative of the magnetic resonance signals produced in examination sequences. The interface circuit 58 may be connected to a control and analysis circuit 60. The control and analysis circuit 60 executes the commands to the driver circuit 50 and RF control circuit 52 based on defined protocols selected via system control circuitry 16.

The control and analysis circuit 60 may also serve to receive the magnetic resonance signals and perform subsequent processing before transmitting the data to system control circuitry 16. Scanner control circuitry 14 may also include one or more memory circuits 62, which store configuration parameters, pulse sequence descriptions, examination results, and so forth, during operation.

A second interface circuit 64 may connect the control and analysis circuit 60 to a system control circuit 66 for exchanging data between scanner control circuitry 14 and system control circuitry 16. The system control circuitry 16 may include a third interface circuit 68, which receives data from the scanner control circuitry 14 and transmits data and commands back to the scanner control circuitry 14. As with the control and analysis circuit 60, the system control circuit 66 may include a computer processing unit (CPU) in a multi-purpose or application specific computer or workstation. System control circuit 66 may include or be connected to a second memory circuit 70 to store programming code for operation of the imaging system 10 and to store the processed image data for later reconstruction, display and transmission. The programming code may execute one or more algorithms that, when executed by a processor, are configured to perform reconstruction of acquired data.

An additional input output (I/O) interface 72 may be provided for exchanging image data, configuration parameters, and so forth with external system components such as remote access and storage systems 18. Finally, the system control circuit 66 may be communicatively coupled to various peripheral devices for facilitating an operator interface and for producing hard copies of the reconstructed images. In the illustrated embodiment, these peripherals include a printer 74, a monitor 76, and a user interface 78 including, for example, devices such as a keyboard, a mouse, a touchscreen (e.g., integrated with the monitor 76), and so forth.

In operation, a user (e.g., a radiologist) may configure and/or oversee control of the imaging system 10. Additionally, the user may assist in positioning the subject (e.g., a patient 26) within the patient bore 22. In some embodiments, the patient bore 22 may surround an entire subject or just a portion thereof (e.g., a patient's head, thorax, and/or extremity). As mentioned above, the RF coils 36 are generally positioned outside of the patient bore 22 proximate to the RF shield 40. However, in an embodiment of the present disclosure, the RF coils 36 may be located on an outer surface of the coil support tube 38 within the shield support tube 42. Imaging may be accomplished on the portion of the patient 26 surrounded by the RF coils 36. As such, the RF coils 36 and/or the coil support tube 38 may extend to any length up to the entire length of the patient bore 22 depending on implementation (e.g., size of subjects to be imaged).

Figure 2:
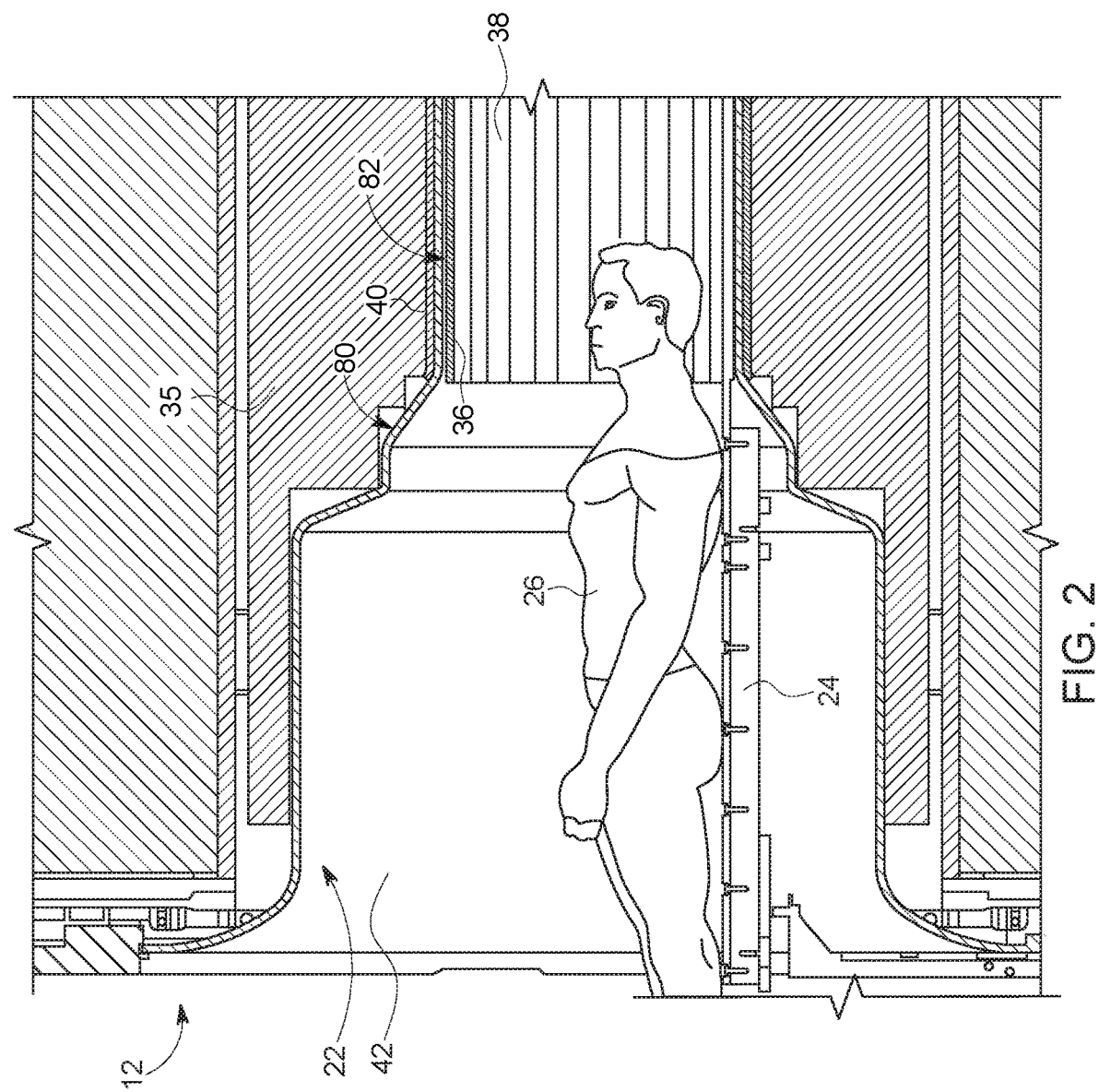
FIG. 2 is a partial cross-sectional elevation view of the MRI system of FIG. 1 having RF coils within a shield support tube and an RF shield outside the shield support tube, in accordance with an aspect of the present disclosure.

To further illustrate, FIG. 2 is a cross-sectional view of the scanner 12 with the RF coils 36 located within the shield support tube 42 and the RF shield 40 positioned outside of the shield support tube 42 (e.g., on an outer surface 80 of the shield support tube 42). Further, the RF coils 36 may be positioned on an outer surface 82 of the coil support tube 38.

In some embodiments, the RF coils 36 and the RF shield 40 may be affixed to the coil support tube 38 and the shield support tube 42, respectively, via one or more fasteners (e.g., clips, screws, etc.) and/or adhesive (e.g., epoxy, surface film adhesive, etc.) The relative position of the RF shield 40 (e.g., between the RF coils 36 and the gradient coils 35) may reduce interaction between the RF coils 36 and the gradient coils 35, as well as shield external components from the electromagnetic fields (e.g., RF fields and magnetic fields). The RF shield 40 may be any suitable type of electromagnetic barrier, for example a conductive mesh (e.g., wire mesh), faraday cage, a series of overlapping capacitive plates, etc. In some embodiments, the use of a wire mesh RF shield 40 and surface film adhesive for securing the RF shield 40 to the exterior of the patient bore 22 may enhance free convective heat transfer from the RF shield 40, for example relative to an RF shield 40 built into the gradient coils 35, for effective cooling.

Additionally, by placing the RF coils 36 within the shield support tube 42, the patient bore 22 overall may have an increased diameter while using the same size gradient coils 35. As such, the patient 26 may have more room within the patient bore 22, especially in areas where there are no RF coils 36 (e.g., in portions defined by the shield support tube 42). A larger patient bore 22 may yield increased patient comfort and/or allow for the imaging of larger subjects.

Figure 3:
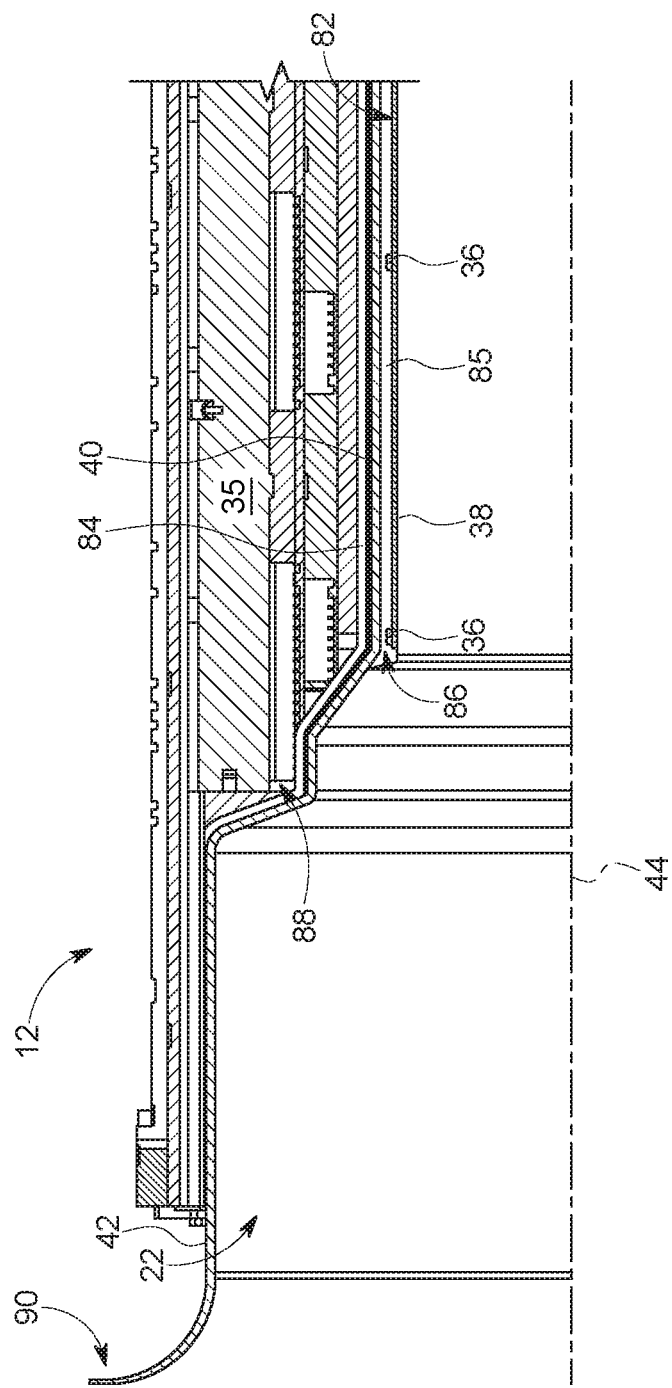
FIG. 3 is an expanded view of the MRI system of FIG. 2 and depicting the position of the RF shield and RF coils relative to other features of the MM system, in accordance with an aspect of the present disclosure.

FIG. 3 is an expanded view of a portion of the scanner 12 illustrating the relative positions and placements of the scanner components. As mentioned above, placing the RF coil 36 within the shield support tube 42 may leave available space between shield support tube 42 and the gradient coils 35, for example, allowing an increase in the size of the shield support tube 42. To maximize the area within the shield support tube 42, for example, to yield space for the patient 26, RF coils 36, and coil support tube 38, a gap 84 between the shield support tube 42 and the gradient coils 35 may be minimized (e.g., less than 50 millimeters (mm), less than 10 mm, or less than 1 mm).

In some embodiments, the gap 84 outside the shield support tube 42 (e.g., on the exterior of the RF shield 40), although minimized, may be used for cooling the gradient coils 35 and/or the RF shield 40. The gap 84, formed between the RF shield 40 and the gradient coils 35, may be arranged to allow a cooling fluid (e.g., gas or liquid) to flow through the gap 84. In some embodiments, ambient or chilled air may be circulated through the gap 84 to cool the RF shield 40 and/or the gradient coils 35 using a blower.

As mentioned above, the coil support tube 38 may be implemented within the shield support tube 42. Additionally, a cooling passage 85 may be situated between the RF coils 36, on the outer surface 82 of the coil support tube 38, and the RF shield 40, on the outer surface 80 of the shield support tube 42. Additionally or alternatively to the gap 84, the cooling passage 85 may allow flow a cooling fluid (e.g., gas or liquid) to cool the RF coils 36, RF shield 40, and/or patient bore 22. For example, the patient bore 22 may become heated by the RF coils 36 and/or the gradient coils 35 effects. Utilizing the cooling passage 85 as a cooling channel (e.g., via a blower or pump) may assist in maintaining a desired temperature of the patient bore 22, for example, for patient comfort.

Placing the shield support tube 42 between the RF coil 36 and RF shield 40 may also increase the distance between the RF coil 36 and the RF shield 40. For example, the distance may be increased by the thickness of the shield support tube 42 and/or the cooling passage 85. The increased distance (e.g., greater than 1 mm, greater than 10 mm, greater than 15, etc.) may alleviate electromagnetic field stresses between the RF coils 36 and the RF shield 40 and allow for more efficient operation of the RF coils 36. The RF shield 40 may reduce electromagnetic interferences within the imaging system 10 by attenuating and/or dampening the electromagnetic fields, for example, generated by the RF coils 36. Such attenuation and dampening may be stronger closer to the RF shield 40. As such, in order to produce an RF field of a particular magnitude, the RF coils 36 may use more power (e.g., electrical current) at distances closer to the RF shield 40. Moreover, when the RF coils 36 are positioned at further distances from the RF shield 40, the amount of electrical current used by the RF coils 36 to generate an the RF field of a particular magnitude may decrease. As such, by positioning the RF coils 36 within the shield support tube 42 (e.g., on a separate tube, the coil support tube 38), the distance between the RF coils 36 and the RF shield 40 may be increased, thus, increasing RF coil efficiency.

Furthermore, in some embodiments, the RF shield 40 may extend along the shield support tube 42 over at least a portion (e.g., 50%, 75%, or 100%) of the length of the RF coils 36 (e.g., the portion of the RF coils 36 adjacent to the patient 26) and/or past an end 86 of the RF coils 36. As mentioned above, the RF shield 40 may assist in reducing unintentional interference between the RF coils 36 and the gradient coils 35 as well as RF interference from the RF coils 36 to other components or devices in the vicinity of the scanner 12. Additionally, the RF shield 40 may assist in attenuating the electromagnetic fields generated by the gradient coils 35 and/or the RF coils 36 in areas within the scanner 12 where such fields may be undesirable. For example, the electromagnetic fields may stimulate nerves and/or muscles of a patient 26, which may result in discomfort. By extending the RF shield 40 into areas past the end 86 of the RF coils 36, the electromagnetic fields in such areas may be reduced and the patient 26 may incur a reduced amount of peripheral nerve stimulation. In some embodiments, the RF shield 40 may extend along a portion of the shield support tube 42 adjacent the subject past the end 86 of the RF coils 36, up to or past an end 88 of the gradient coil 35, and/or up to an end 90 of the shield support tube 42.

Additionally, the decreased interference between the gradient coils 35 and the RF coils 36 due to the extended RF shield 40 may reduce the amount of tuning performed during initial setup of the imaging system 10. Proper tuning of the RF coils 36 and gradient coils 35 may yield clearer and/or more accurate imaging results. However, tuning can be an extensive and/or time consuming endeavor. As such, the reduction in electromagnetic interference leading to a reduction in tuning due to the extended RF shield 40 may help decrease costs and/or time associated with imaging system tuning.

Tuning may also be sensitive to the relative positions of the RF coils 36 and the RF shield 40. As stated above, in traditional configurations, the RF shielding may be incorporated into the gradient coils 35. In such a case, if the RF coils 36 are moved or removed from within the gradient coils 35 and/or the RF shielding, the scanner 12 may need to be retuned. However, by placing the RF shield 40 on the outer surface 80 of the shield support tube 42 and the RF coils 36 on a separate coil support tube 38, the RF coils 36 on the coil support tube 38 and the RF shield 40 on the shield support tube 42 may each form a modular element of the scanner 12 that may be tuned together outside the gradient coils 35. That is, the shield support tube 42 may be removable from within the gradient coils 35 and the coil support tube 38 may be removable from within the shield support tube 42, for example, to facilitate simplified servicing of the gradient coils 35, RF coils 36 and/or RF shield 40. Additionally or alternatively, in some embodiments, the shield support tube 42 and the coil support tube 38 may have a fixed relative positional orientation such that the coil support tube 38 may be repeatable removed and replaced within the shield support tube 42 with the same relative orientation. For example, a track system and/or alignment indicators (e.g., lines, arrows, etc.) on the shield support tube 42 and/or coil support tube 38 may help with placement of the RF coils 36 in the same relative position (e.g., relative to the RF shield 40) to reduce retuning.

Figure 4:
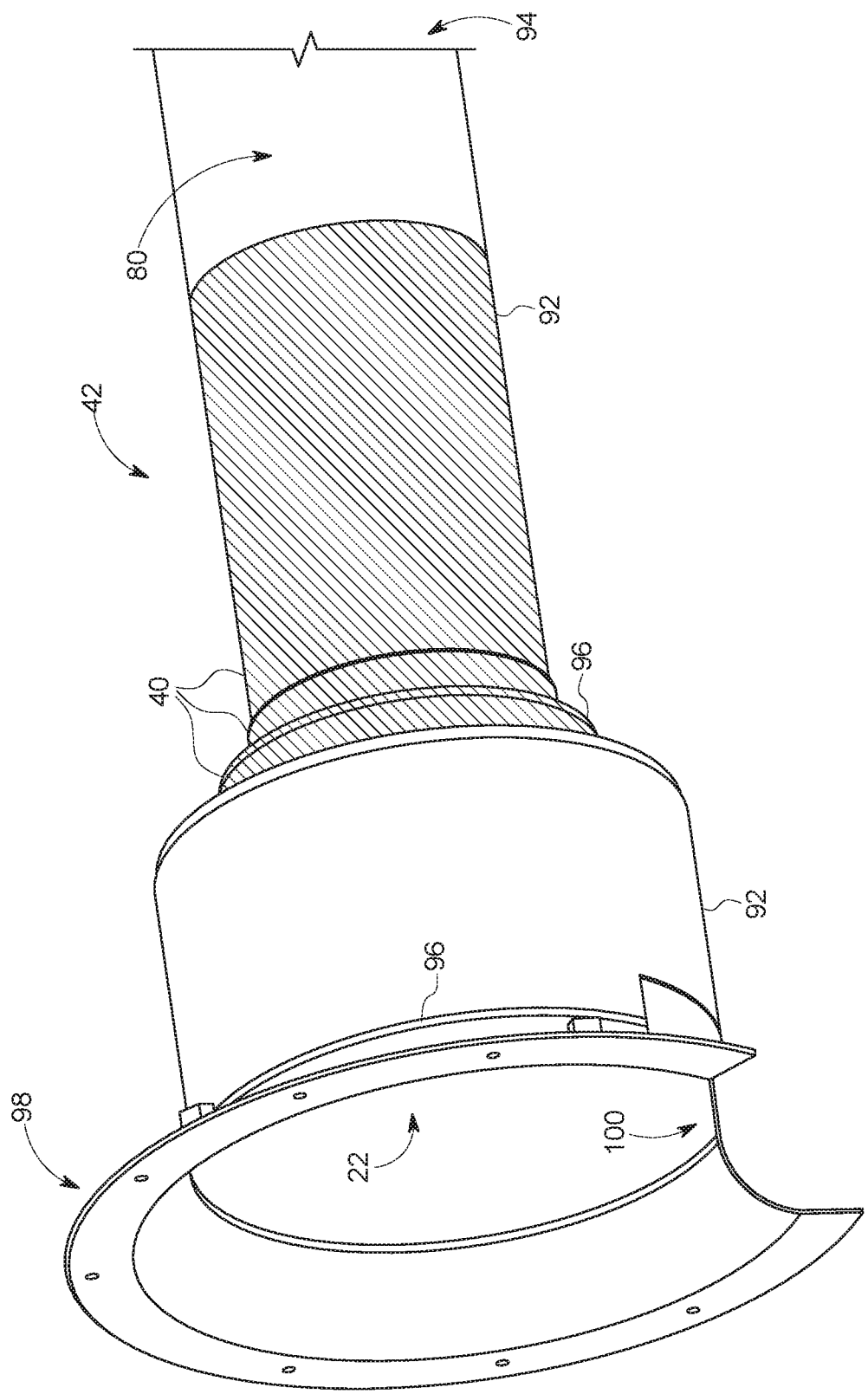
FIG. 4 is a perspective view of a modular patient bore having an RF shield on the exterior of a shield support tube, in accordance with an aspect of the present disclosure.

To help further illustrate, FIG. 4 is a perspective view of one embodiment of the shield support tube 42 removed from within the gradient coils 35 with an RF shield 40 attached to the outer surface 80. In some embodiments, the shield support tube 42 may be removed from within the gradient coils 35 along with the coil support tube 38. As such, the relative position of the RF coils 36 and the RF shield 40 may not change. In maintaining this relative position, repeated tuning of the RF coils 36 with the RF shield 40 may be reduced or eliminated. For example, in some scenarios, it may be desirable to remove the shield support tube 42 and coil support tube 38 from within the gradient coils 35 for servicing of the scanner 12. When removed and replaced, the RF coils 36 and the RF shield 40 may maintain the same relative positions due to being mounted on modular supports (e.g., the shield support tube 42 and coil support tube 38), thus, reducing and/or eliminating retuning. Further, the RF coil 36 and the RF shield 40 may be affixed to their respective supports and the coil support tube 38 inserted into the shield support tube 42 before being inserted into the scanner 12 (e.g., within the gradient coils 35) and therefore tuned outside the scanner 12. Tuning outside the scanner 12 may allow for further simplified tuning, for example, by making the RF coils 36 and/or RF shield 40 more accessible. Additionally, a modular embodiment of the patient bore 22 with the RF shield 40 mounted to the outer surface 80 of the shield support tube 42 may ease assembly and/or servicing of the scanner 12. For example, instead of incorporating the RF shield 40 into/onto the gradient coils 35, the RF shield 40 may be more easily removed within the scanner 12.

The modular nature of the patient bore 22 also allows for different shapes of patient bores 22 to be fitted within the scanner 12. Different shapes may be implemented because each patient bore 22 may already have a matched RF coil 36 and RF shield 40 and, thus, is not dependent on shielding within the gradient coils 35 or elsewhere in the scanner 12. Additionally or alternatively, the patient bore 22 may be pieced together from multiple bore tubes of one or more shapes (e.g., multiple sections of shield support tubes 42 and/or coil support tubes 38. As such, any suitable shape (e.g., cylindrical, spherical, flared, rectangular, trumpet, or a combination thereof) may be implemented within the scanner 12. Some shapes of patient bores 22 may have increased suitability for shielding effects. For example, the illustrated trumpet-shaped patient bore 22 may allow for reduced peripheral nerve stimulation effects from gradient coil pulsing by allowing the RF shield 40, which, for example, may extend to the end of the gradient coil 35, to flare at an angle relative to the axis 44 of the patient bore 22.

As discussed above, the shield support tube 42 and/or coil support tube 38 may include one or more pieces to produce different size and/or shaped patient bores 22. As should be appreciated, the shield support tube 42 and the coil support tube 38 may also be formed as single pieces in any suitable shape. In one embodiment, the shield support tube 42 may include one or more cylindrical sections 92 (e.g., annular sections) with a scanner end 94 to be inserted into the scanner 12 (e.g., surrounded by the gradient coils 35). To produce the trumpet shape, one or more flares 96 may change the diameter of the shield support tube 42. For example, the flares 96 may increase the diameter of the patient bore 22 from the scanner end 94 towards a patient end 98 (e.g., from where the patient 26 enters the patient bore 22). Additionally, some of the cylindrical sections 92 and/or flares 96 may have a cutout 100, for example, to accommodate the table 24. In accordance with one aspect of the disclosure, the RF coils 36 may be implemented within the cylindrical section 92 adjacent the scanner end 94 and the RF shield 40 may be affixed to the outer surface 80 of the shield support tube 42 and extend past the RF coils 36 in the direction of the scanner end 94 and/or the patient end 98. Further, the RF shield 40 may also be implemented on the flares 96. In a similar manner to the shield support tube 42, the coil support tube 38 may include cylindrical sections, flares, and/or other suitable shapes. Moreover, the RF coils 36 may be mounted on a cylindrical section of the coil support tube 38 and/or the other shaped sections, if present.

Figure 5:
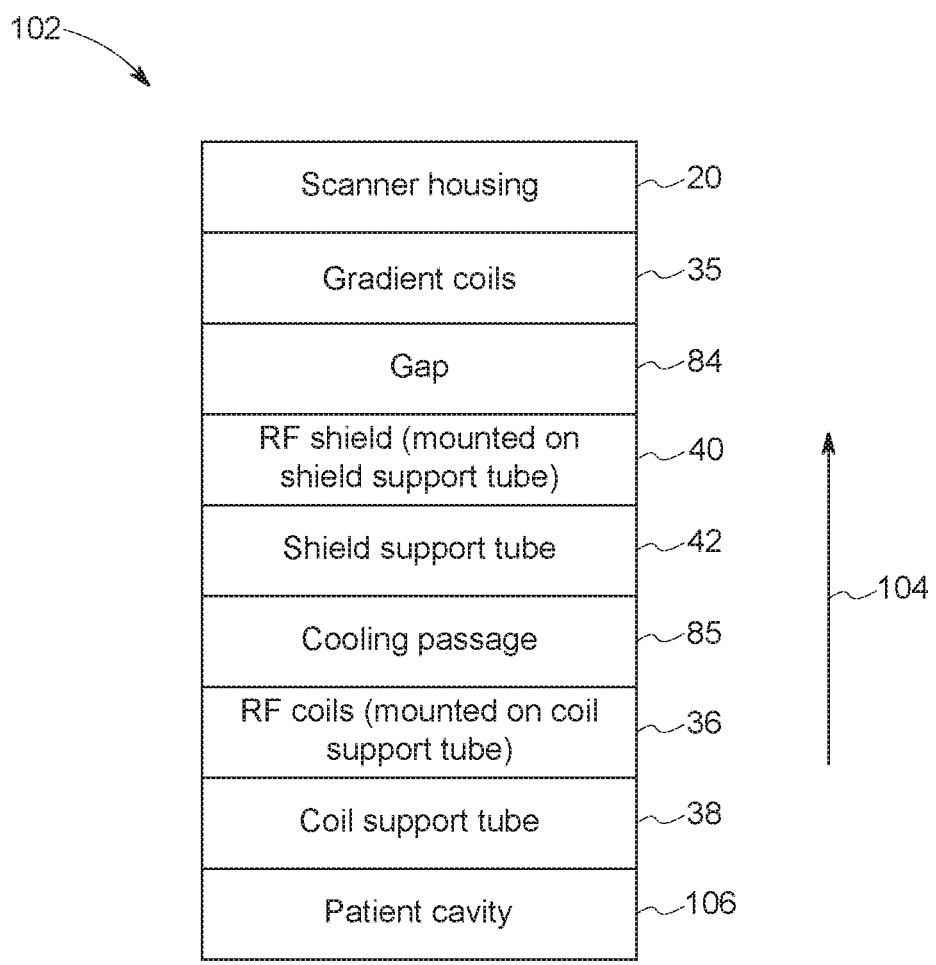
FIG. 5 is an example radial stackup of some of the layers of the MM system, in accordance with an aspect of the present disclosure.

In one embodiment, the scanner 12 may include a trumpet-shaped modular patient bore 22 including the shield support tube 42, with the RF shield 40 affixed to the outer surface 80, and the coil support tube 38, with the RF coil 36 fixed to the outer surface 82. Additionally, the RF shield 40 may extend along the outer surface 80 of the shield support tube 42 past the end 86 of the RF coils 36. Such a scanner 12 may yield increased power efficiency, reduced maintenance, and/or increased patient comfort. In further illustration of one such embodiment, FIG. 5 is a radial stackup 102 depicting some of the layers of the assembled scanner 12 in a radial direction 104 (e.g., from a patient cavity 106 within the patient bore 22 to the exterior of the scanner 12). In the illustrated embodiment, the coils support tube 38 may surround a patient cavity 106, and the RF coils 36 may be mounted on the outer surface 82 of the coil support tube 38. There may also be the cooling passage 85 between the RF coils 36 and the shield support tube 42, on which the RF shield 40 is mounted, for example to provide cooling to the RF coils 36, the RF shield 40 and/or the patient bore and/or to expand the distance between the RF coils 36 and the RF shield 40. In some embodiments, sections of the patient cavity 106 may be surrounded directly by the shield support tube 42, for example, in sections of the patient bore 22 where there is no coil support tube 38. The gap 84 may be between the RF shield 40 and the gradient coils 35. In some embodiments, cooled air or other fluid may be flowed through the cooling passage 85 the gap 84, both, or neither. Moreover, the housing 20 of the scanner 12 may encompass the gradient coils 35 and that which lies within.

Figure 6:
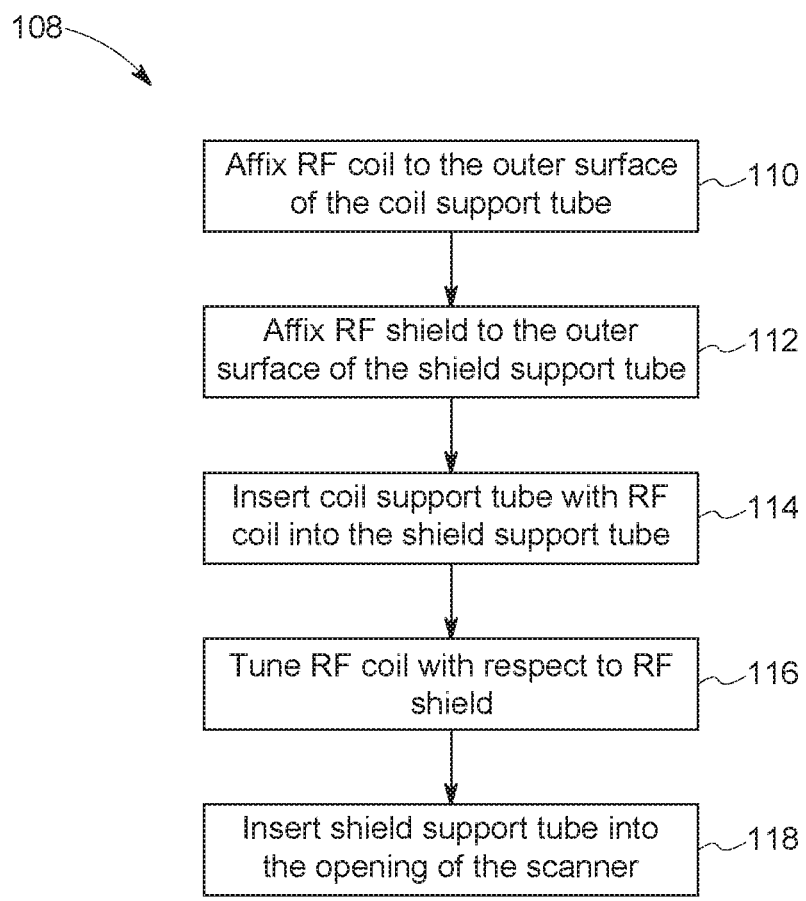
FIG. 6 is a flowchart of an example process for assembling a modular patient bore within the MRI system of FIG. 1, in accordance with an aspect of the present disclosure.

FIG. 6 is a flowchart 108 of an example process for assembling a modular patient bore 22 within the imaging system 10. The RF coil 36 may be affixed to the outer surface 82 of the coil support tube 38 (process block 110). Additionally, the RF shield 40 may be affixed to the outer surface 80 of the shield support tube 42 (process block 112). The coil support tube 38 with the RF coil 36 may be inserted into the shield support tube 42 (process block 114). The RF coil 36 may then be tuned with respect to the RF shield 40 (process block 116). The shield support tube 42 may be inserted into the opening of the scanner 12 (process block 118) surrounded by the gradient coils 35. As should be appreciated, in accordance with the present disclosure, tuning may occur before or after the shield support tube 42 and coil support tube 38 are inserted into the scanner 12. Although the above referenced flowchart 108 is shown in a given order, in certain embodiments, the depicted steps may be reordered, altered, deleted, and/or occur simultaneously. Additionally, the referenced flowchart 108 is given as an illustrative tool, and further decision and/or process blocks may be added depending on implementation.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging device comprising:
  a patient bore configured to house a subject to be imaged, wherein the patient bore comprises one or more bore tubes;
  a gradient coil surrounding, at least partially, the patient bore;
  a radio frequency (RF) shield located outside a bore tube of the one or more bore tubes; and
  an RF coil located within the bore tube of the one or more bore tubes.

2. The imaging device of claim 1, wherein the one or more bore tube comprises a shield support tube, wherein the RF shield is mounted to an outer surface of the shield support tube.

3. The imaging device of claim 2, comprising a cooling passage between the RF coil and the shield support tube, wherein a blower is configured to flow air through the cooling passage.

4. The imaging device of claim 2, wherein the shield support tube comprises a trumpet shape comprising one or more cylindrical sections and one or more flared sections.

5. The imaging device of claim 2, wherein the one or more bore tubes comprises a coil support tube, wherein the RF coil is mounted to an outer surface of the coil support tube.

6. The imaging device of claim 5, wherein the shield support tube and the coil support tube comprise concentric cylinders.

7. The imaging device of claim 1, wherein the RF shield extends axially along the patient bore beyond an end of the RF coil.

8. The imaging device of claim 1, wherein the RF shield extends at least to a first end of the RF coil and at least to a second end of the RF coil, wherein the first end and the second end are on opposite sides of the RF coil in an axial direction corresponding to the patient bore.

9. The imaging device of claim 1, wherein the RF shield comprises an electrically conductive mesh.

10. The imaging device of claim 1, wherein the imaging device comprises a magnetic resonance imaging system.

11. A patient bore configured to surround a subject for imaging, the patient bore comprising:
  a shield support tube;
  a coil support tube configured to be removably inserted into the shield support tube;
  a radio frequency (RF) coil mounted to a first outer surface of the coil support tube; and an RF shield mounted to a second outer surface of the shield support tube, wherein the RF shield is configured to reduce RF interference to or from the RF coil.

12. The patient bore of claim 11, comprising a flare configured to change a diameter of the shield support tube from a first diameter to a second diameter.

13. The patient bore of claim 12, wherein the RF shield extends, at least, onto the flare.

14. The patient bore of claim 11, wherein the coil support tube is configured to house a head of the subject.

15. The patient bore of claim 11, wherein the patient bore is a modular patient bore configured to be inserted into a magnetic resonance imaging scanner.

16. The patient bore of claim 15, wherein the RF coil is configured to be tuned with the RF shield while outside the magnetic resonance imaging scanner.

17. The patient bore of claim 15, wherein the RF coil is configured to be removed from the magnetic resonance imaging scanner and reinserted without retuning the RF coil.

18. A magnetic resonance imaging system comprising:
a patient bore configured to house a subject, the patient bore comprising:
a shield support tube;
a coil support tube configured to be removably inserted into the shield support tube;
a radio frequency (RF) coil configured to generate an RF signal, wherein the RF coil is mounted on a first surface of the coil support tube; and
an RF shield configured to attenuate the RF signal, wherein the RF shield is mounted to a second surface of the shield support tube; and
a gradient coil configured to generate a magnetic field, wherein the gradient coil comprises a cavity configured to house the patient bore, wherein the RF signal, the magnetic field, or a combination thereof operatively cause excitation within the subject, wherein the excitation is measured by the magnetic resonance imaging system to compute an image corresponding to the subject.

19. The magnetic resonance imaging system of claim 18, wherein, during operation, a cooling fluid is configured to flow in a cooling passage formed between the RF coil and the RF shield.

20. The magnetic resonance imaging system of claim 18, wherein the patient bore is configured to fill the cavity to minimize a gap between the gradient coil and the patient bore.

* * * * *